US007006682B1

(12) United States Patent
Moriya et al.

(10) Patent No.: US 7,006,682 B1
(45) Date of Patent: Feb. 28, 2006

(54) APPARATUS FOR MONITORING PARTICLES AND METHOD OF DOING THE SAME

(75) Inventors: Tsuyoshi Moriya, Tokyo (JP); Fumihiko Uesugi, Tokyo (JP); Natsuko Ito, Tokyo (JP)

(73) Assignee: NEC Corporation, Tokyo (JP)

( * ) Notice: Subject to any disclaimer, the term of this patent is extended or adjusted under 35 U.S.C. 154(b) by 500 days.

(21) Appl. No.: 09/656,713

(22) Filed: Sep. 7, 2000

(30) Foreign Application Priority Data

Sep. 9, 1999 (JP) .............................. 11-255320

(51) Int. Cl.
*G06K 9/00* (2006.01)
(52) U.S. Cl. ...................... 382/145; 382/190; 382/273; 356/335; 356/337; 700/108; 700/121; 438/16; 250/261
(58) Field of Classification Search ............... 382/141, 382/145, 190, 192, 194, 205, 271, 273; 348/86, 348/87; 700/95, 108, 109, 121; 438/16; 356/335–337, 237.3, 237.5
See application file for complete search history.

(56) References Cited

U.S. PATENT DOCUMENTS

| 4,263,508 | A | * | 4/1981 | Leary et al. ............. 250/358.1 |
| 4,633,714 | A | * | 1/1987 | Mazumder et al. ......... 356/336 |
| 4,740,708 | A | * | 4/1988 | Batchelder ............. 250/559.41 |
| 4,798,465 | A | * | 1/1989 | Knollenberg ............... 356/336 |
| 4,830,494 | A | * | 5/1989 | Ishikawa et al. ............ 356/336 |
| 5,316,983 | A | * | 5/1994 | Fujimori et al. ............ 356/335 |
| 5,471,298 | A | * | 11/1995 | Moriya ....................... 356/336 |
| 5,576,827 | A | * | 11/1996 | Strickland et al. .......... 356/336 |
| 5,861,951 | A | * | 1/1999 | Uesugi et al. .............. 356/338 |
| 5,870,189 | A | * | 2/1999 | Uesugi et al. .............. 356/335 |
| 5,929,980 | A | * | 7/1999 | Yamaguchi et al. ....... 356/4.03 |
| 5,946,092 | A | * | 8/1999 | DeFreez et al. ............ 356/336 |
| 6,366,690 | B1 | * | 4/2002 | Smilansky et al. ......... 382/149 |
| 6,368,567 | B1 | * | 4/2002 | Comita et al. .......... 423/240 R |

FOREIGN PATENT DOCUMENTS

| JP | 4-54440 | 2/1992 |
| JP | 5-273110 | 10/1993 |

(Continued)

OTHER PUBLICATIONS

Uesugi et al., "Real-time monitoring of scattered laser light by a single particle of several tens of nanometers in the etching chamger in relation to its status with the equipment," J Vac Sci Techn. A 16(3), May/Jun. 1998, p. 1189-1195.*

(Continued)

*Primary Examiner*—Bhavesh M. Mehta
*Assistant Examiner*—Manav Seth
(74) *Attorney, Agent, or Firm*—Sughrue Mion, PLLC

(57) ABSTRACT

There is provided an apparatus for monitoring a size of a particle, including (a) a laser beam source which radiates a laser beam to an area in which particles exist, (b) a photodetector which receives the laser beam having been scattered by the particles, and outputs image data including brightness of pixels, (c) an area detector which detects pixels corresponding to an area on which the scattered laser beam is incident, based on the image data, (d) a maximum brightness detector which detects a maximum brightness among brightness of the pixels detected by the area detector, and (e) a measurement unit which compares the maximum brightness to a predetermined threshold brightness to thereby measure a relative size of the particles.

81 Claims, 10 Drawing Sheets

FOREIGN PATENT DOCUMENTS

| | | | |
|---|---|---|---|
| JP | 6-82358 | | 3/1994 |
| JP | 7-55692 | | 3/1995 |
| JP | 9-243549 | | 9/1997 |
| JP | 10-10036 | * | 1/1998 |
| JP | 10010036 A | * | 1/1998 |
| JP | 10-232196 | * | 9/1998 |
| JP | 10232196 A | * | 9/1998 |
| JP | 11-44654 | * | 2/1999 |

OTHER PUBLICATIONS

G.S. Selwyn, "Plasma Particulate Contamination Control. I. Transport and Process Effects", J. Vac. Sci. Technol. B 9 (6), Nov./Dec. 1991, pp. 3487-3492.

* cited by examiner

APPARATUS FOR MONITORING PARTICLES AND METHOD OF DOING THE SAME

BACKGROUND OF THE INVENTION

1. Field of the Invention

The invention relates to an apparatus of monitoring particles generated in fabrication of a semiconductor device, through the use of a laser beam, and a method of doing the same. More particularly, the invention relates to such an apparatus which is capable of monitoring particles at realtime by utilizing a scattered laser beam, and a method of doing the same.

2. Description of the Related Art

While a semiconductor device is being fabricated, there are generated particles such as dusts in a fabrication room. If such particles are adhered to a semiconductor device, performances of the semiconductor device would be much deteriorated. Hence, various apparatuses for monitoring particles have been developed in order to know the reason why such particles are generated in a fabrication room or the mechanism of generating such particles, or control an apparatus for fabricating a semiconductor device, to depress generation of such particles.

Examples of a particle monitoring system are described in Journal of Vacuum Science and Technology, Vol. B9, 1991, pp. 3487–3492, and Journal of Vacuum Science and Technology, Vol. A14, 1996, pp. 649–654, both written by Gary S. Selwyn.

The above-mentioned particle monitoring system is illustrated in FIG. 1.

As illustrated in FIG. 1, the particle monitoring system is comprised of a reaction chamber 15 formed with an beam-introduction window 16 and a detection window 17, a laser beam source 11, an oscillation mirror 13 reflecting a laser beam radiated from the laser beam source 11 into the reaction chamber 15, a photodetector 12 detecting a laser beam scattered by particles 19 existing in the reaction chamber 15, and a beam damper 18 absorbing a laser beam radiated from the laser beam source 11 and not scattered by the particles 19.

The particle monitoring system operates as follows.

A laser beam radiated from the laser beam source 11 is reflected at the oscillation mirror 13, and directed into the reaction chamber 15 through the introduction window 16. When the laser beam collides with the particles 19, the laser beam is scattered. The scattered laser beam is detected by the photodetector 12 such as a charge coupled device (CCD) camera through the detection window 17.

The detected scattered laser beam is recorded as a dynamic image indicative of the time at which the laser beam was scattered, and how an intensity of the scattered laser beam varied. Thus, it is possible to know how the particles 19 have been generated.

Apart from the above-mentioned particle monitoring system, an apparatus and/or method of monitoring particles generated in a room in which a semiconductor device is to be fabricated are suggested in Japanese Unexamined Patent Publications Nos. 4-54440, 5-273110, 6-82358, 9-243549, and 7-55692.

Japanese Unexamined Patent Publication No. 4-54440 has suggested an apparatus for monitoring particles, in which two laser beams are scanned by means of a rotary mirror. The laser beams having been scattered by particles are detected by a photodetector, and presence or absence of particles and speed of particles are measured based on the detection.

Japanese Unexamined Patent Publication No. 5-273110 has suggested an apparatus for measuring a diameter of a particle sufficient small relative to a wavelength of a laser beam. In the apparatus, a maximum scattering intensity is measured based on scattering intensity of each of pixels, using image data of scattered laser beams. Then, a diameter of a particle is calculated, based on the fact that an integration scattering intensity is in proportion to both the maximum scattering intensity and sixth power of a diameter of a particle.

Japanese Unexamined Patent Publication No. 6-82358 has suggested an apparatus for monitoring particles. In the apparatus, red, green and blue laser beams are radiated to particles. A size of a particle can be calculated based on how the laser beams are scattered in dependence on a wavelength of the laser beams and a size of a particle. Observing a color of the scattered laser beam through a monitor television, a size of a particle is measured.

Japanese Unexamined Patent Publication No. 9-243549 has suggested a method of monitoring particles. Laser beams are scanned to particles, and then, the laser beams having been scattered by particles are detected. In accordance with the method, data about three-dimensional distribution of particles can be obtained by means of a plurality of laser beam sources and a plurality of photodetectors for detecting scattered laser beams.

Japanese Unexamined Patent Publication No. 7-55692 has suggested an apparatus for monitoring particles, including a first vacuum chamber formed around a second vacuum chamber in which a semiconductor device is fabricated. The first vacuum chamber is in fluid communication with the second chamber, and is formed with a first window through which a laser beam is introduced thereinto and a second window through which a scattered laser beam leaves the first vacuum chamber.

In order to effectively control behavior of particles generated in a room in which a semiconductor device is fabricated, it is necessary to know data about a size and the number of particles in a real-time.

However, the above-mentioned particle monitoring system is accompanied with a problem that since particles are monitored through dynamic images of the detected, scattered laser beam, if images of particle are quite complex in the dynamic images, it would be quite difficult to obtain data about a size and the number of particles in a real-time.

Though the apparatus suggested in Japanese Unexamined Patent Publication No. 4-54440 can detect presence or absence of particles and a speed of particles, the apparatus cannot detect a size of individual particles which is a key for realizing the reason why particles are generated.

In the apparatus suggested in Japanese Unexamined Patent Publication No. 5-273110, it is necessary to calculate a sixth power root of the maximum scattering intensity in order to calculate a size of a particle, based on the measured maximum scattering intensity.

In the apparatus suggested in Japanese Unexamined Patent Publication No. 6-82358, data about a size of a particle is obtained in accordance with a color displayed in a monitor television. Accordingly, if obtained images of particles are complicated, it would be quite difficult to accurately grasp a size of a particle. In addition, a complicated device would be necessary for analyzing a color, and hence, it would take much time to analyze a color, resulting in that it would be impossible to have data about particles in a real-time.

The method suggested in Japanese Unexamined Patent Publication No. 9-243549 is accompanied with a problem that an apparatus used in the method cannot avoid to be large in a size, because the apparatus has to include a plurality of laser beam sources and a plurality of photodetectors.

The apparatus suggested in Japanese Unexamined Patent Publication No. 7-55692 is accompanied with a problem that the first vacuum chamber has to be additionally formed apart from the second vacuum chamber in which a semiconductor device is fabricated.

SUMMARY OF THE INVENTION

In view of the above-mentioned problems in the conventional apparatuses and methods of monitoring particles, it is an object of the present invention to provide an apparatus and a method both of which are capable of providing various data about particles in a real-time.

In one aspect of the present invention, there is provided an apparatus for monitoring a size of a particle, including (a) a laser beam source which radiates a laser beam to an area in which particles exist, (b) a photodetector which receives the laser beam having been scattered by the particles, and outputs image data including brightness of pixels, (c) an area detector which detects pixels corresponding to an area on which the scattered laser beam is incident, based on the image data, (d) a maximum brightness detector which detects a maximum brightness among brightness of the pixels detected by the area detector, and (e) a measurement unit which compares the maximum brightness to a predetermined threshold brightness to thereby measure a relative size of the particles.

In accordance with the apparatus, it is possible to have a relative size of a particle merely by comparing a maximum brightness to a predetermined threshold brightness. Hence, it would take quite a short time to have a relative size of a particle, ensuring that data about a size of a particle is obtained in a real-time.

It is preferable that the area detector first determines a threshold brightness to which brightness of pixels are to be compared, judges whether a brightness of a pixel is equal to or greater than the threshold brightness, and determines pixels located adjacent to each other among pixels having been judged to have a brightness equal to or greater than the threshold brightness, as pixels corresponding to an area on which a laser beam scattered by a particle is incident.

The apparatus may further include a second measurement unit which measures an intensity of the scattered laser beam, based on the maximum brightness, and measures a relative size of the particles, based on the intensity of the scattered laser beam, in accordance with an equation which defines a relation between an intensity of a scattered laser beam and a relative size of particles.

Herein, the particles are ones which are generated in fabrication of a semiconductor device. The apparatus may further include a third measurement unit which judges whether the relative size of the particles is greater than a predetermined threshold size in order to judge whether the particles would exert harmful influence on a semiconductor device, and which ceases fabrication of a semiconductor device, if the relative size of the particles has been judged to be greater than the predetermined threshold size.

It is preferable that the apparatus further includes a scanner which scans the laser beam emitted from the laser beam source.

It is preferable that the photodetector includes a charge coupled device camera comprised of a plurality of light-receiving devices arranged in a matrix.

It is preferable that the apparatus further includes a particle counter which counts up each time the particle counter receives a signal from the area detector, and transmits a signal indicative of a count, to the measurement unit.

It is preferable that the apparatus further includes a heater for heating a chamber in which the particle is generated, to remove by-products from the chamber.

There is further provided an apparatus for monitoring a size of a particle, including (a) a laser beam source which radiates a laser beam to an area in which particles exist, (b) a photodetector receiving the laser beam having been scattered by the particles, and outputting image data including brightness of pixels, (c) an area detector which detects pixels corresponding to an area on which the scattered laser beam is incident, based on the image data, (d) a counter which counts the number of the pixels detected by the area detector, and (e) a measurement unit which compares the number of the pixels to a predetermined threshold number to thereby measure a relative size of the particles.

In accordance with the apparatus, it is possible to have a relative size of a particle merely by comparing the number of particles to a predetermined threshold number. Hence, it would take quite a short time to have a relative size of a particle, ensuring that data about a size of a particle is obtained in a real-time.

There is still further provided an apparatus for monitoring a size of a particle, including (a) a laser beam source which radiates a laser beam to an area in which particles exist, (b) a photodetector receiving the laser beam having been scattered by the particles, and outputting image data including brightness of pixels, (c) an area detector which detects pixels corresponding to an area on which the scattered laser beam is incident, based on the image data, (d) a calculator which calculates a total of brightness of the pixels detected by the area detector, and (e) a measurement unit which compares the total to a predetermined threshold brightness to thereby measure a relative size of the particles.

In accordance with the apparatus, it is possible to have a relative size of a particle merely by comparing a total of brightness to a predetermined threshold brightness. Hence, it would take quite a short time to have a relative size of a particle, ensuring that data about a size of a particle is obtained in a real-time.

For instance, the calculator may be comprised of (d1) a maximum brightness detector which detects a maximum brightness among brightness of the pixels detected by the area detector, and (d2) a counter which counts the number of the pixels detected by the area detector, in which case, the measurement unit compares the maximum brightness or the number of the pixels to a predetermined threshold brightness or a predetermined threshold number to thereby measure a relative size of the particles.

As an alternative, the calculator may be comprised of (d1) a maximum brightness detector which detects a maximum brightness among brightness of the pixels detected by the area detector, and (d2) a counter which counts the number of the pixels detected by the area detector, in which case, the measurement unit uses the total and at least one of the maximum brightness an the number of the pixels for measuring a relative size of the particles.

There is yet further provided an apparatus for monitoring a size of a particle, including (a) a laser beam source which radiates a laser beam to an area in which particles exist, (b) a photodetector receiving the laser beam having been scattered by the particles, and outputting image data including brightness of pixels, (c) an area detector which detects pixels corresponding to an area on which the scattered laser beam is incident, based on the image data, (d) a first measurement unit which measures an intensity of the scattered laser beam, based on brightness of the pixels detected by the area detector, and (e) a second measurement unit which measures a relative size of the particles, based on the intensity of the scattered laser beam, in accordance with an equation which defines a relation between an intensity of a scattered laser beam and a relative size of particles.

In accordance with the above-mentioned apparatus, it is possible to measure an actual size of a particle, based on an intensity of the scattered laser beam. Hence, if the measured particles are ones which are generated in fabrication of a semiconductor device, it would be possible to foresee how a semiconductor device being fabricated is influenced by the particles.

It is preferable that the second measurement unit includes a memory which stores a software program used for calculating a size of a particle in accordance with the equation of Rayleigh scattering, and a threshold size to which a calculated size is to be compared.

For instance, the threshold size may be designed to be equal to or smaller than a minimum diameter among diameters of wirings in a semiconductor device to be fabricated.

In another aspect of the present invention, there is provided a method of monitoring a size of a particle, including the steps of (a) radiating a laser beam to an area in which particles exist, (b) receiving the laser beam having been scattered by the particles, and outputting image data including brightness of pixels, (c) detecting pixels corresponding to an area on which the scattered laser beam is incident, based on the image data, (d) detecting a maximum brightness among brightness of the pixels detected in the step (c), and (e) comparing the maximum brightness to a predetermined threshold brightness to thereby measure a relative size of the particles.

In accordance with the method, it is possible to have a relative size of a particle merely by comparing a maximum brightness to a predetermined threshold brightness. Hence, it would take quite a short time to have a relative size of a particle, ensuring that data about a size of a particle is obtained in a real-time.

For instance, the step (c) may include the steps of (c1) determining a threshold brightness to which brightness of pixels are to be compared, (c2) judging whether a brightness of a pixel is equal to or greater than the threshold brightness, and (c3) determining pixels located adjacent to each other among pixels having been judged to have a brightness equal to or greater than the threshold brightness, as pixels corresponding to an area on which a laser beam scattered by a particle is incident.

It is preferable that the method further include the steps of measuring an intensity of the scattered laser beam, based on the maximum brightness, and measuring a relative size of the particles, based on the intensity of the scattered laser beam, in accordance with an equation which defines a relation between an intensity of a scattered laser beam and a relative size of particles.

Herein, the particles are ones which are generated in fabrication of a semiconductor device. The method may further include the steps of judging whether the relative size of the particles is greater than a predetermined threshold size in order to judge whether the particles would exert harmful influence on a semiconductor device, and ceasing fabrication of a semiconductor device, if the relative size of the particles has been judged to be greater than the predetermined threshold size.

It is preferable that the method further includes the step of heating a chamber in which the particles are generated, for removing by-products from the chamber.

It is preferable that the method further includes the step of scanning the laser beam.

It is preferable that the method further includes the step of counting up each time of receiving a signal transmitted in the step (c), and transmitting a signal indicative of a count.

There is further provided a method of monitoring a size of a particle, including the steps of (a) radiating a laser beam to an area in which particles exist, (b) receiving the laser beam having been scattered by the particles, and outputting image data including brightness of pixels, (c) detecting pixels corresponding to an area on which the scattered laser beam is incident, based on the image data, (d) counting the number of the pixels detected in the step (c), and (e) comparing the number of the pixels to a predetermined threshold number to thereby measure a relative size of the particles.

In accordance with the method, it is possible to have a relative size of a particle merely by comparing the number of particles to a predetermined threshold number. Hence, it would take quite a short time to have a relative size of a particle, ensuring that data about a size of a particle is obtained in a real-time.

There is still further provided a method of monitoring a size of a particle, including the steps of (a) radiating a laser beam to an area in which particles exist, (b) receiving the laser beam having been scattered by the particles, and outputting image data including brightness of pixels, (c) detecting pixels corresponding to an area on which the scattered laser beam is incident, based on the image data, (d) calculating a total of brightness of the pixels detected in the step (c), and (e) comparing the total to a predetermined threshold brightness to thereby measure a relative size of the particles.

In accordance with the method, it is possible to have a relative size of a particle merely by comparing a total of brightness to a predetermined threshold brightness. Hence, it would take quite a short time to have a relative size of a particle, ensuring that data about a size of a particle is obtained in a real-time.

There is yet further provided a method of monitoring a size of a particle, including the steps of (a) radiating a laser beam to an area in which particles exist, (b) receiving the laser beam having been scattered by the particles, and outputting image data including brightness of pixels, (c) detecting pixels corresponding to an area on which the scattered laser beam is incident, based on the image data, (d) measuring an intensity of the scattered laser beam, based on brightness of the pixels detected in the step (c), and (e) measuring a relative size of the particles, based on the intensity of the scattered laser beam, in accordance with an equation which defines a relation between an intensity of a scattered laser beam and a relative size of particles.

In accordance with the above-mentioned method, it is possible to measure an actual size of a particle, based on an intensity of the scattered laser beam. Hence, if the measured particles are ones which are generated in fabrication of a semiconductor device, it would be possible to foresee how a semiconductor device being fabricated is influenced by the particles.

In still another aspect of the present invention, there is provided a recording medium readable by a computer, storing a program therein for causing a computer to act as an apparatus for monitoring a size of a particle, the apparatus including (a) an area detector which detects pixels corresponding to an area on which a laser beam having been scattered by particles is incident, based on image data including brightness of pixels, output by a photodetector receiving the scatted laser beam, (b) a maximum brightness detector which detects a maximum brightness among brightness of the pixels detected by the area detector, and (c) a measurement unit which compares the maximum brightness to a predetermined threshold brightness to thereby measure a relative size of the particles.

There is further provided a recording medium readable by a computer, storing a program therein for causing a computer to act as an apparatus for monitoring a size of a particle, the apparatus including (a) an area detector which detects pixels corresponding to an area on which a laser beam having been scattered by particles is incident, based on image data including brightness of pixels, output by a photodetector receiving the scatted laser beam, (b) a counter which counts the number of the pixels detected by the area detector, and (c) a measurement unit which compares the number of the pixels to a predetermined threshold number to thereby measure a relative size of the particles.

There is still further provided a recording medium readable by a computer, storing a program therein for causing a computer to act as an apparatus for monitoring a size of a particle, the apparatus including (a) an area detector which detects pixels corresponding to an area on which a laser beam having been scattered by particles is incident, based on image data including brightness of pixels, output by a photodetector receiving the scatted laser beam, (b) a calculator which calculates a total of brightness of the pixels detected by the area detector, and (c) a measurement unit which compares the total to a predetermined threshold brightness to thereby measure a relative size of the particles.

There is yet further provided a recording medium readable by a computer, storing a program therein for causing a computer to act as an apparatus for monitoring a size of a particle, the apparatus including (a) an area detector which detects pixels corresponding to an area on which a laser beam having been scattered by particles is incident, based on image data including brightness of pixels, output by a photodetector receiving the scatted laser beam, (b) a first measurement unit which measures an intensity of the scattered laser beam, based on brightness of the pixels detected by the area detector, and (c) a second measurement unit which measures a relative size of the particles, based on the intensity of the scattered laser beam, in accordance with an equation which defines a relation between an intensity of a scattered laser beam and a relative size of particles.

There is still yet further provided a recording medium readable by a computer, storing a program therein for causing a computer to carry out a method of monitoring a size of a particle, the method including the steps of (a) detecting pixels corresponding to an area on which a laser beam having been scattered by particles is incident, based on image data including brightness of pixels, output by a photodetector receiving the scatted laser beam, (b) detecting a maximum brightness among brightness of the pixels detected in the step (a), and (c) comparing the maximum brightness to a predetermined threshold brightness to thereby measure a relative size of the particles.

There is further provided a recording medium readable by a computer, storing a program therein for causing a computer to carry out a method of monitoring a size of a particle, the method including the steps of (a) detecting pixels corresponding to an area on which a laser beam having been scattered by particles is incident, based on image data including brightness of pixels, output by a photodetector receiving the scatted laser beam, (b) counting the number of the pixels detected in the step (a), and (c) comparing the number of the pixels to a predetermined threshold number to thereby measure a relative size of the particles.

There is further provided a recording medium readable by a computer, storing a program therein for causing a computer to carry out a method of monitoring a size of a particle, the method including the steps of (a) detecting pixels corresponding to an area on which a laser beam having been scattered by particles is incident, based on image data including brightness of pixels, output by a photodetector receiving the scatted laser beam, (b) calculating a total of brightness of the pixels detected in the step (a), and (c) comparing the total to a predetermined threshold brightness to thereby measure a relative size of the particles.

There is further provided a recording medium readable by a computer, storing a program therein for causing a computer to carry out a method of monitoring a size of a particle, the method including the steps of (a) detecting pixels corresponding to an area on which a laser beam having been scattered by particles is incident, based on image data including brightness of pixels, output by a photodetector receiving the scatted laser beam, (b) measuring an intensity of the scattered laser beam, based on brightness of the pixels detected in the step (c), and (c) measuring a relative size of the particles, based on the intensity of the scattered laser beam, in accordance with an equation which defines a relation between an intensity of a scattered laser beam and a relative size of particles.

The advantages obtained by the aforementioned present invention will be described hereinbelow.

As will be obvious to those skilled in the art, in accordance with the present invention, it is possible to measure a relative size of a particle merely by comparing the number of pixels, the maximum brightness and a total of brightness to the threshold values, respectively. Thus, it is now possible to measure a relative size of a particle by the apparatus having a simple structure, and shorten a time for measuring a relative size of a particle.

It is also possible to measure an actual size of a particle, based on an intensity of the scattered laser beam. Hence, if the measured particles are ones which are generated in fabrication of a semiconductor device, and have such a size to exert harmful influence on a semiconductor device, it would be possible to stop fabrication of a semiconductor device. Accordingly, it would be possible to enhance a yield in fabrication of a semiconductor device.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained hereinbelow with reference to drawings.

First Embodiment

Figure 1:
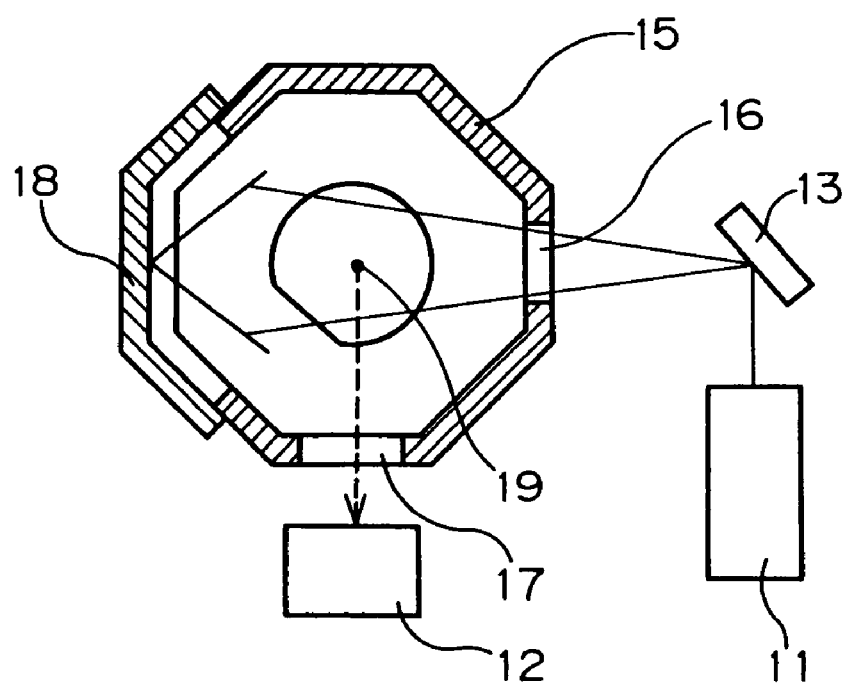
FIG. 1 is a cross-sectional view of a conventional particle monitor system.
Figure 2:
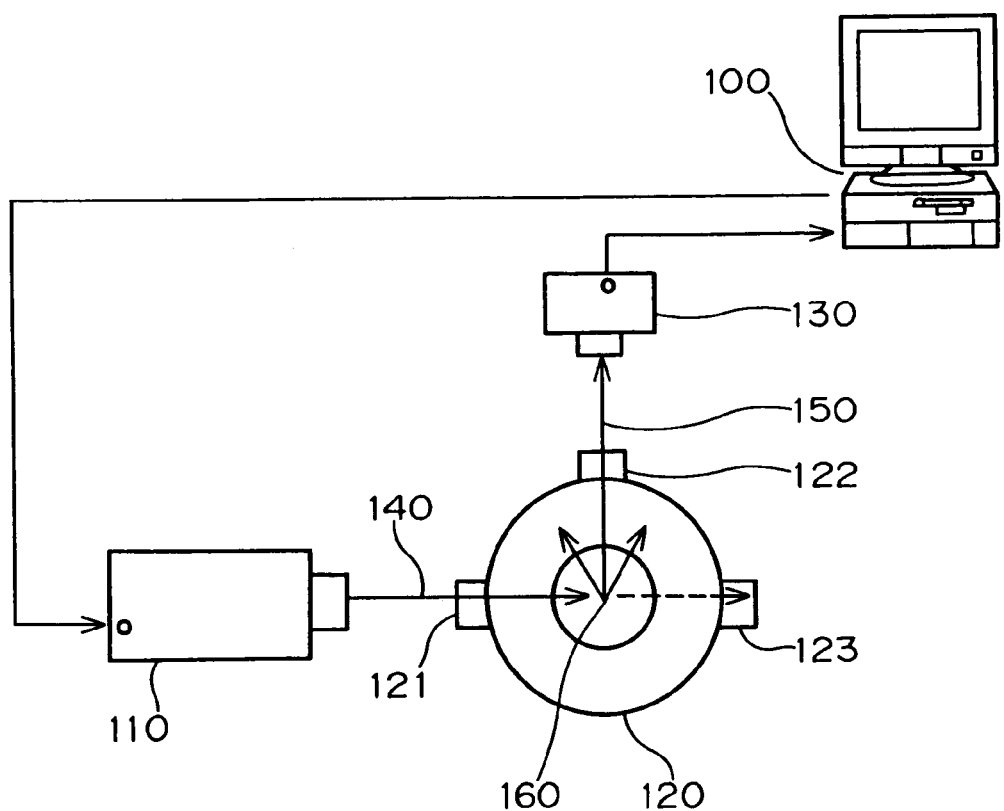
FIG. 2 illustrates a particle monitor system in accordance with the first embodiment of the present invention.

FIG. 2 illustrates a particle monitoring system in accordance with the first embodiment of the present invention.

The particle monitoring system is comprised of a computer 100, a laser beam source 110, a chamber 120 in which a semiconductor device is fabricated and particles 160 are generated, and a photodetector 130 which detects a laser beam scattered by the particles 160.

The computer 100 has the same functions as those of a central processing unit, such as transfer of data, control of a program, and control of the system. Specifically, the computer 100 controls the particle monitoring system, and processes monitored data.

The laser beam source 110 radiates a laser beam 140 into the chamber 120 in response to a control signal transmitted from the computer 100. The laser beam 140 is radiated into the chamber 120 in the same area as a cross-sectional area of the laser beam 140. Some of particles generated in the chamber 120 exist in the radiation area of the laser beam 140. Hence, it is not always necessary to scan the laser beam 140.

The number of particles generated in the chamber 120 is calculated by multiplying the number of particles per a cross-sectional area of the laser beam 140 by a ratio defined as X/Y wherein X indicates a cross-sectional area of the chamber 120 and Y indicates a cross-sectional area of the laser beam 140. It should be noted that the thus calculated number of particles is an approximate value, and hence, the laser beam 140 is necessary to be controlled to have such a cross-sectional area to ensure requisite accuracy.

A semiconductor device is fabricated in the chamber 120. While a semiconductor device is being fabricated in the chamber 120, particles such as dust are generated in the chamber 120, causing defectiveness in a semiconductor device:

The chamber 120 is formed with a first window 121 through which the laser beam 140 is introduced thereinto and a second window 122 through which a laser beam 150 having been scattered by the particles 160 leaves the chamber 120. The chamber 120 is equipped with a beam absorber 123 in facing relation to the first window 121. The laser beams 140 having been not scattered by the particles 160 are absorbed to the beam absorber 123.

Figure 3:
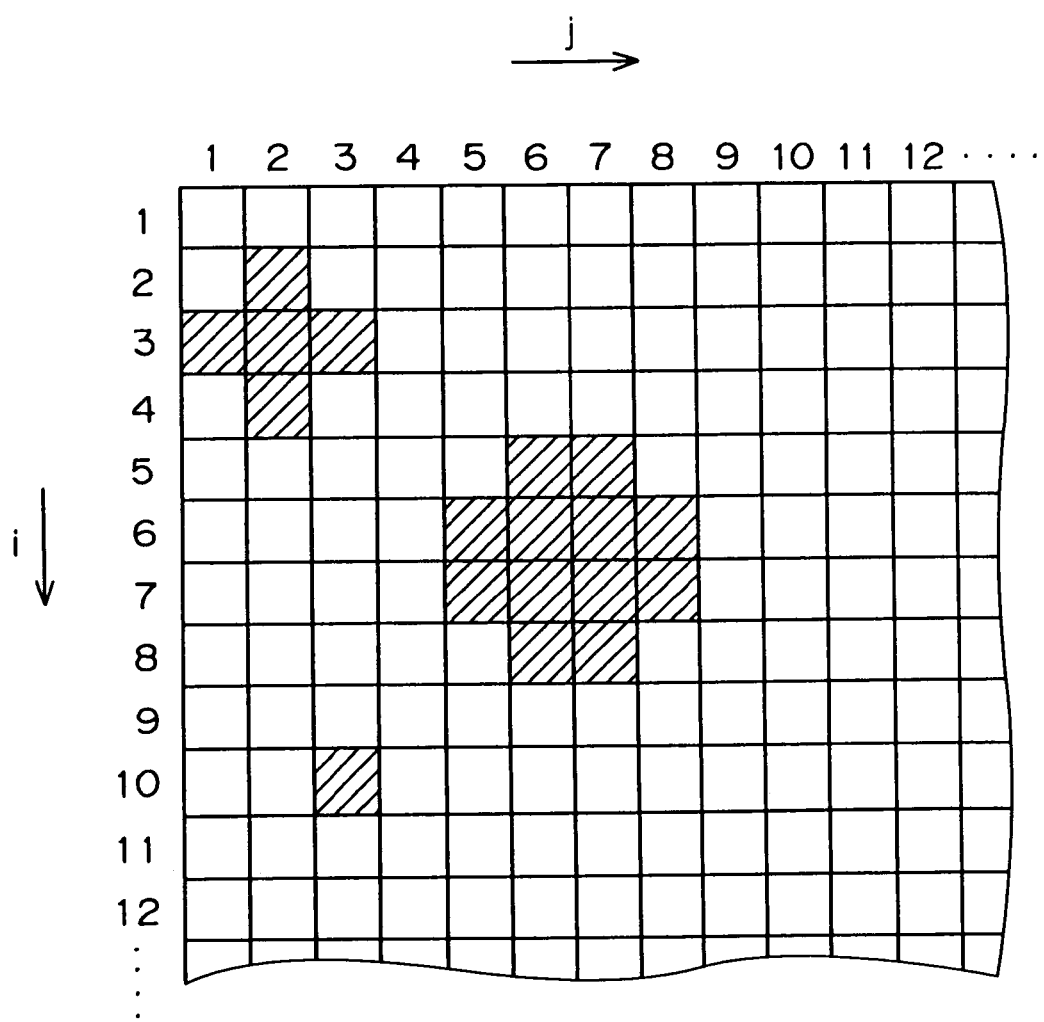
FIG. 3 illustrates pixels some of which detect reflected laser beams.

The photodetector 130 is comprised of a charge coupled device (CCD) camera including a plurality of light-receiving devices arranged in a matrix. The photodetector 130 detects the scattered laser beam 150 leaving the chamber 120, and outputs the thus detected scattered laser beam 150 to the computer 100 as two-dimensional image data. This two-dimensional image data includes both coordinates indicative of a location of a pixel, and a brightness of the pixel. For instance, an image of the scattered laser beam 150 detected by the CCD camera 130 is comprised of a plurality of pixels, each of which is illustrated as a square in FIG. 3. Each of the pixels in FIG. 3 is identified with a pair of coordinates (i, j).

Hereinbelow is explained a structure of the computer 100.

Figure 4:
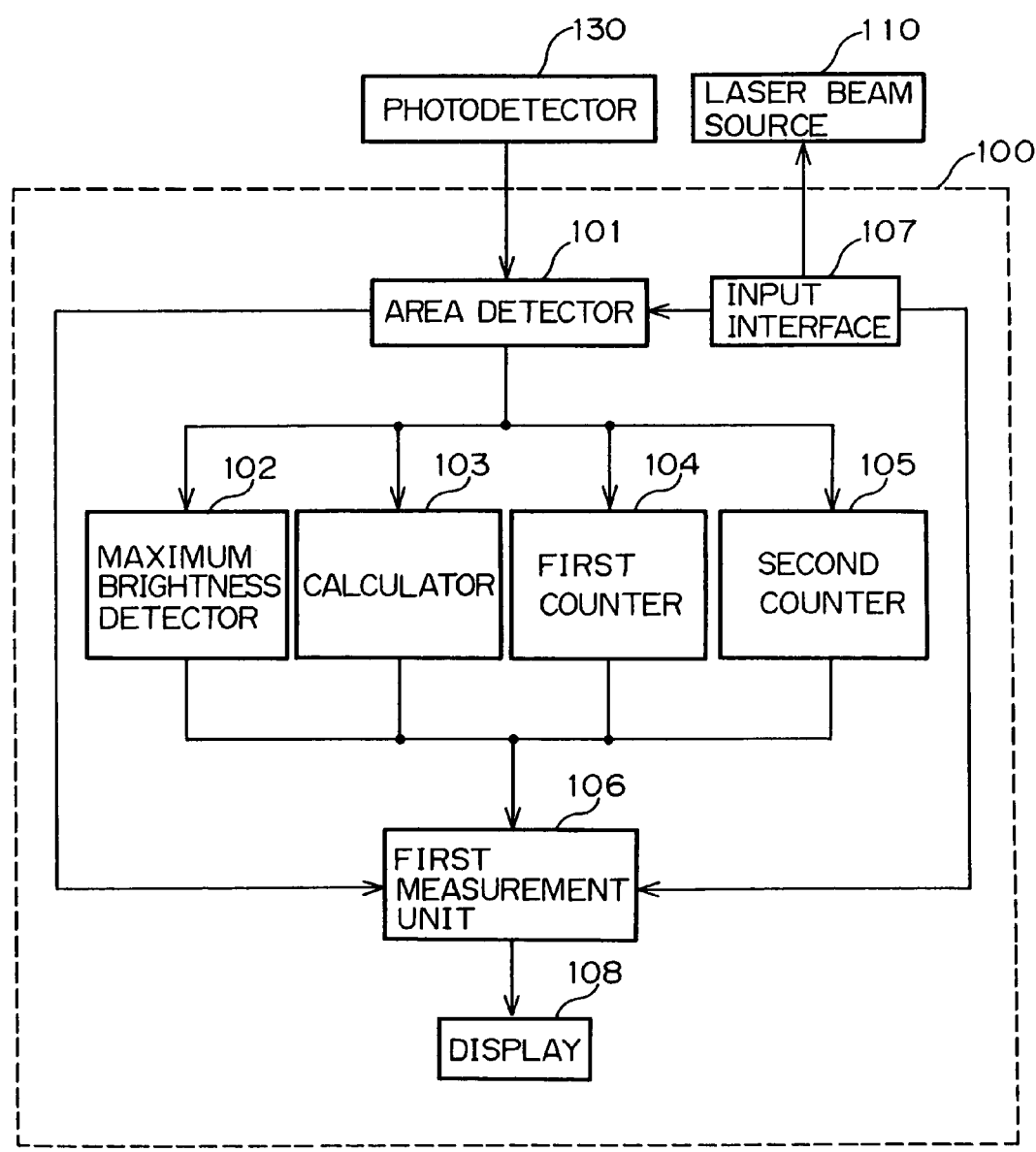
FIG. 4 is a block diagram of a computer constituting the particle monitor system in accordance with the first embodiment.

As illustrated in FIG. 4, the computer 100 is comprised of an area detector 101, a maximum brightness detector 102 detecting a maximum brightness among brightness of pixels detected by the area detector 101, a calculator 103 calculating a total of brightness of pixels detected by the area detector 101, a first counter 104 counting the number of pixels detected by the area detector 101, a second counter 105 counting the number of particles generated in the chamber 120, a first measurement unit 106, an input interface 107, and a display 108.

The area detector 101 includes a memory (not illustrated) in which a threshold brightness input from the input interface 107 is stored therein. The area detector 101 compares the two-dimensional image data input from the photodetector 130, to the threshold brightness stored in the memory to thereby process the two-dimensional image data in a later mentioned manner, and resultingly, detects a group of pixels each having a brightness equal to or greater than the threshold brightness. Hereinbelow, such a group of pixels is referred to as a high brightness pixel area.

The area detector 101 identifies a location of the high brightness pixel area and brightness of each of the pixels in the high brightness pixel area, and transmits them to the maximum brightness detector 102, the calculator 103, the first counter 104 and the second counter 105 as data about pixels having high brightness.

When the area detector 101 cannot detect the high brightness pixel area, the area detector 101 transmits a zero-signal to the first measurement unit 106 which zero-signal indicates that there does not exist the high brightness pixel area.

The maximum brightness detector 102 detect a maximum brightness among brightness of pixels in the high brightness pixel area, based on data about pixels having high brightness, transmitted from the area detector 101, and transmits the thus detected maximum brightness detector 102 to the first measurement unit 106.

The calculator 103 calculates a total of brightness of pixels in the high brightness pixel area, based on data about pixels having high brightness, transmitted from the area detector 101, and transmits the thus calculated total f brightness to the first measurement unit 106.

The first counter 104 counts the number of pixels in the high brightness pixel area, based on data about pixels having high brightness, transmitted from the area detector 101, and transmits the thus counted number of pixels to the first measurement unit 106.

The second counter 105 counts up each time data about pixels having high brightness is transmitted from the area detector 101, and transmits a count to the first measurement unit 106. Herein, a count as an output signal transmitted from the second counter 105 indicates the number of the particles 160.

A degree at which the laser beam 140 is scattered by the particles 160 is dependent on a size of the particles 160. Hence, the maximum brightness transmitted from the maximum brightness detector 102, a total of brightness transmitted from the calculator 103, and the number of particles transmitted from the first counter 104 each indicates a size of the particles 160. The count transmitted from the second counter 105 indicates the number of the particles 160.

The first measurement unit 106 includes a memory (not illustrated) in which a threshold maximum brightness, a threshold total of brightness and a threshold number of pixels all input from the input interface 107 are stored. The first measurement unit 106 compares the maximum brightness input from the maximum brightness detector 102, the total of brightness input from calculator 103 and the number of pixels input from the first counter 104 to the threshold values stored in the memory, to thereby measure a relative size of the particles 160.

Then, the first measurement unit 106 multiplies a size of the particles measured based on each of data, by a weighing factor input from the input interface 107 to thereby calculate a relative size of the particles 160. Then, the first measurement unit 106 transmits the thus calculated size of the particles 160 to the display 108.

When the first measurement unit 106 receives the zero-signal from the area detector 101, the first measurement unit 106 transmits the number of the particles 160 input from the second counter 105, to the display 108.

The input interface 107 includes a keyboard (not illustrated) through which a threshold value which the area detector 101 uses to process the two-dimensional image data, and reference data which the first measurement unit 106 uses to measure a relative size of the particles 160 are input.

When a predetermined key in the keyboard is actuated, the input interface 107 transmits control signals by which the laser beam source 110, the area detector 101 and the first measurement unit 106 are controlled.

The display 108 displays a size of the particles 160 and the number of the particles 160 and other data all input from the first measurement unit 106.

Hereinbelow is explained an operation of the above-mentioned particle monitor system.

First, an operator actuates a predetermined key in the keyboard or input interface 107. In response to the actuation of the predetermined key, the input interface 107 transmits a signal to the laser beam source 110 to instruct the laser beam source 110 to radiate the laser beams 140. Then, the laser beam source 110 radiates the laser beams 140 to the chamber 120.

The laser beams 140 introduced into the chamber 120 through the first window 121 would be scattered, if the particles 160 exist on an optical path of the laser beams 140. The scattered laser beam 150 leaves the chamber 120 through the second window 122, and is received in the photodetector 130.

The scattered laser beam 150 is received in the photodetector 130 comprised of a charge coupled device (CCD) camera, and is output to the computer 100 as two-dimensional image data.

On receipt of the two-dimensional data from the photodetector 130, the computer 100 starts retrieval of pixels.

Figure 5:
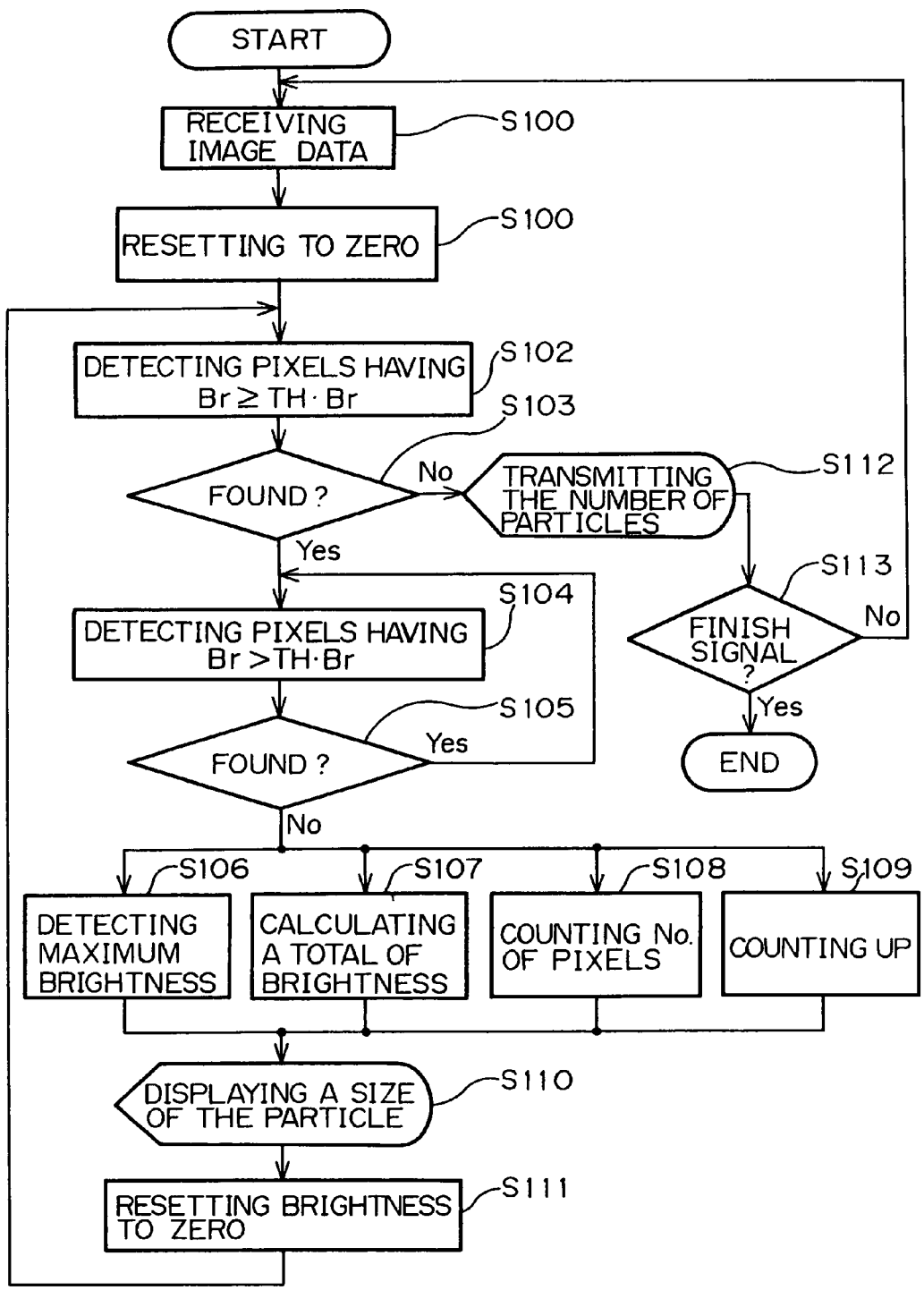
FIG. 5 is a flow chart of pixel retrieval to be carried out by a computer constituting the particle monitor system in accordance with the first embodiment.

FIG. 5 is a flow-chart showing an operation of retrieving pixels, carried out by the computer 100.

The area detector 101 receives the two-dimensional image data transmitted from the photodetector 130, in step S100.

The area detector 101 compares brightness of each of pixels indicated in the received two-dimensional image data to a threshold brightness which has been in advance input into the area detector 101 from the input interface 107, and then, resets brightness smaller than the threshold brightness, to zero, in step S101.

Then, the area detector 101 scans the pixels one by one, based on the two-dimensional image data, to thereby detect pixels having a brightness equal to or greater than the threshold brightness, in step S102. In scanning the pixels, the area detector 101 scans the pixels in the order of (1, 1), (1, 2), - - - , (1, n), (2, 1), (2, 2), - - - , (2, n), for instance, in FIG. 3.

If a pixel X having a brightness equal to or greater than the threshold brightness is found (YES in step S103), the area detector 101 further tries to find pixels which are located adjacent to the previously detected pixel X and which has a brightness equal to or greater than the threshold brightness, in step S104.

It is now supposed in FIG. 3 that the hatched squares indicate pixels each having a brightness equal to or greater than the threshold brightness. The area detector 101 starts scanning first the pixel located at (1, 1). As a result, the area detector 101 first finds the pixel located at (2, 2) as a pixel having a brightness equal to or greater than the threshold brightness. Then, the area detector 101 further tries to find a pixel having a brightness equal to or greater than the threshold brightness, among the pixels located at (1, 2), (2, 1), (2, 3), and (3, 2) all located adjacent to the pixel located at (2, 2).

If a pixel Y having a brightness equal to or greater than the threshold brightness, among the pixels located at (1, 2), (2, 1), (2, 3), and (3, 2) (YES in step S105), the area detector 101 carries out the step S104 again. That is, the area detector 101 tries to find a pixel having a brightness equal to or greater than the threshold brightness, among pixels located adjacent to the pixel Y, in step S104. The pixels having been found as a pixel a brightness equal to or greater than the threshold brightness are not searched by the area detector 101 in secondly carrying out the step S104.

Specifically, with reference to FIG. 3, the area detector 101 first finds the pixel located at (3, 2) as the pixel Y in step S104, and returns to the step S104. Then, the area detector 101 tries to find a pixel having a brightness equal to or greater than the threshold brightness, among the pixels located at (3, 1), (3, 3) and (4, 2) all located adjacent to the pixel located at (3, 2).

If a pixel having a brightness equal to or greater than the threshold brightness is not found (NO in step S105), the area detector 101 transmits data indicative of both coordinates and brightness of the pixels having been detected so far which pixels have a brightness equal to or greater than the threshold brightness, to the maximum brightness detector 102, the calculator 103, the first counter 104 and the second counter 105.

Herein, a group of the pixels having been found as pixels having a brightness equal to or greater than the threshold brightness and located adjacent to one another, which group was previously defined as the high brightness pixel area, indicates an area consisting of pixels into which the laser beam scattered by a particle was incident.

The maximum brightness detector 102 detects a maximum brightness among brightness of pixels located in the high brightness pixel area, based on the data received from the area detector 101, in step S106.

The calculator 103 calculates a total of brightness of pixels located in the high brightness pixel area, based on the data received from the area detector 101, in step S107.

The first counter 104 counts the number of pixels located in the high brightness pixel area, based on the data received from the area detector 101, in step S108.

The second counter 105 counts up one by one on receipt of the data transmitted from the area detector 101, in step S109. Since the data about the pixels having a brightness equal to or greater than the threshold brightness, transmitted from the area detector 101, relates to the laser beam 150 scattered by one particle, a count indicated by the second counter 105 indicates the number of particles having been detected by the area detector 101.

The maximum brightness detected by the maximum brightness detector 102, the total of brightness calculated by the calculator 103, and the number of pixels counted by the first counter 104 are transmitted to the first measurement unit 106.

The count counted by the second counter 105 is transmitted to the first measurement unit 106 as data indicative of the number of particles. This data is displayed in the display 108 to show the number of particles, as mentioned later.

The first measurement unit 106 compares the thus received maximum brightness, total of brightness, and number of pixels to the threshold values to thereby calculate a relative size of a particle, based on each of data.

Then, the first measurement unit 106 multiplies a size of the particles calculated based on each of data, by a predetermined weighing factor input from the input interface 107 to thereby calculate an average size of the particles. Then, the first measurement unit 106 transmits the thus calculated average size of the particles to the display 108 for displaying the average size therein, in step S110.

After outputting the data about the pixels having a brightness equal to or greater than the threshold brightness, the area detector 101 resets the brightness of the pixels located in the detected high brightness pixel area, to zero, in step S111, and then, returns to the step S102. Since the brightness of the detected pixels has been reset to zero in step S111, when pixels are scanned in step S102, a pixel which is to be first detected as a pixel having a brightness equal to or greater than the threshold brightness is the pixel located at (5, 6) in FIG. 3.

The above-mentioned steps are repeatedly carried out until it is judged in step S103 that there does not exist a pixel having a brightness equal to or greater than the threshold brightness.

If a pixel having a brightness equal to or greater than the threshold brightness is not found (NO in step S103), the area detector 101 transmits a zero-signal which indicates that there does not exist a pixel having a brightness equal to or greater than the threshold brightness, to the first measurement unit 106.

When the first measurement unit 106 receives the zero-signal from the area detector 101, the first measurement unit 106 transmits the number of the particles 160 input from the second counter 105, to the display 108 for displaying the number of the particles 160, in step S112.

Then, the area detector 101 judges whether a user of the particle monitoring system actuates a predetermined key in the input interface 107 for inputting a finish signal indicating that the steps to detect the pixels are to be finished, in step S113.

When the finish signal is not input through the input interface 107 (NO in step S113), the step S100 is carried out again. That is, the area detector 101 receives the non-processed two-dimensional image data again.

When the finish signal is input through the input interface 107 (YES in step S113), the area detector 101 finishes the steps of detecting the pixels without receiving the two-dimensional image data.

The finish signal is transmitted to the laser beam source 110 from the input interface 107. In response to the finish signal, the laser beam source 140 finishes radiating the laser beams 140.

As mentioned above, the steps S100 to S113 are repeatedly carried out after a predetermined key in the input interface 107 is actuated, until the finish signal is transmitted.

In accordance with the first embodiment, data about a size of a particle is displayed in the display 108 of the computer 100 at a real-time. Hence, a user of the particle monitoring system can know at a real-time how much size a particle has. Accordingly, a user can control an apparatus for fabricating a semiconductor device such that there are less generated particles in the apparatus.

Second Embodiment

Figure 6:
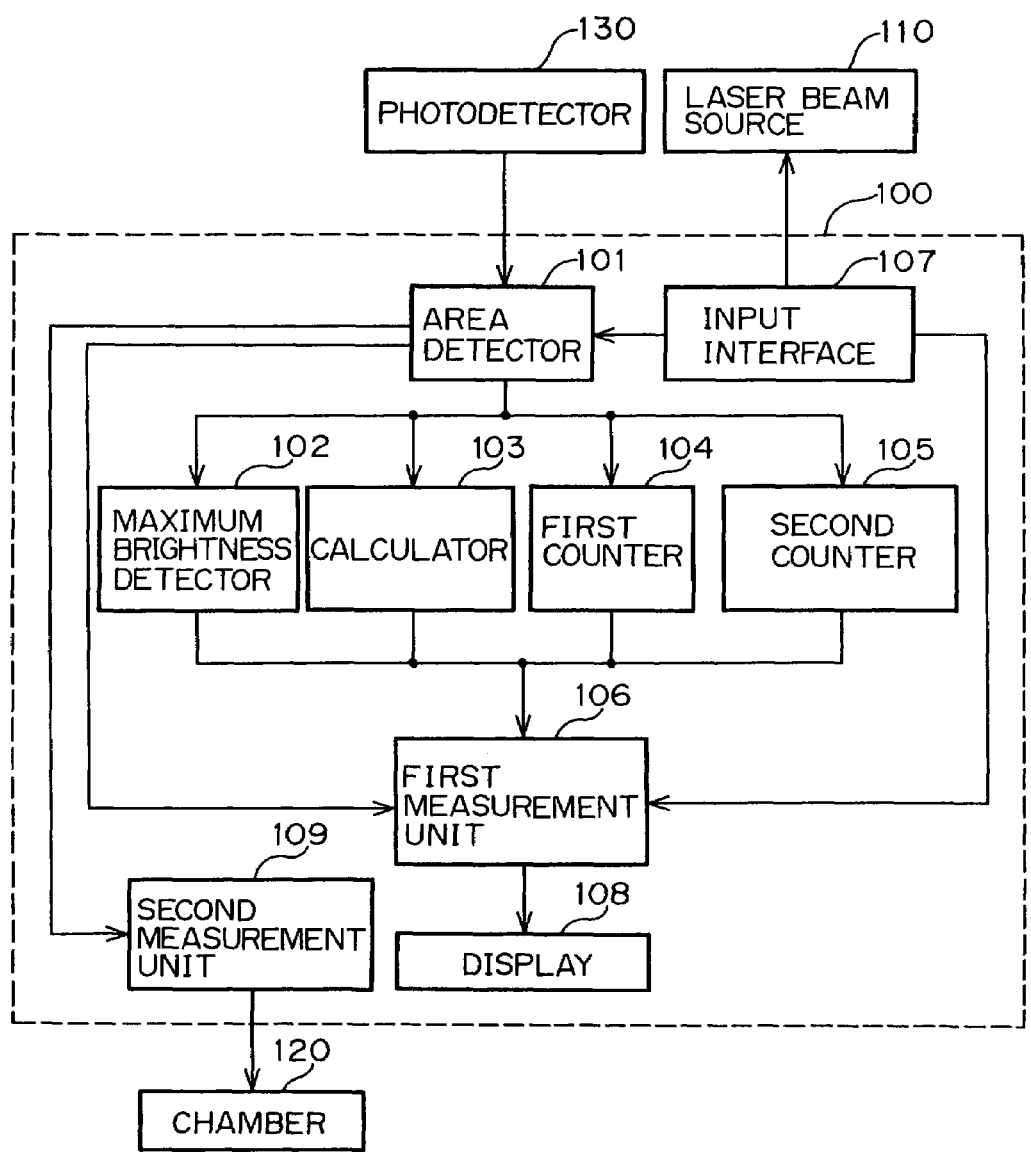
FIG. 6 is a block diagram of a computer constituting the particle monitor system in accordance with the second embodiment.

FIG. 6 is a block diagram of the particle monitoring system in accordance with the second embodiment.

The particle monitoring system in accordance with the second embodiment is comprised of a computer 100, a laser beam source 110, a chamber 120 in which a semiconductor device is fabricated and particles 160 are generated, and a photodetector 130 which detects a laser beam scattered by the particles 160.

As illustrated in FIG. 6, the computer 100 is comprised of an area detector 101, a maximum brightness detector 102 detecting a maximum brightness among brightness of pixels detected by the area detector 101, a calculator 103 calculating a total of brightness of pixels detected by the area detector 101, a first counter 104 counting the number of pixels detected by the area detector 101, a second counter 105 counting the number of particles generated in the chamber 120, a first measurement unit 106, an input interface 107, a display 108, and a second measurement unit 109.

In comparison with the particle monitoring system in accordance with the first embodiment, illustrated in FIG. 4, the particle monitoring system in accordance with the second embodiment additionally includes the second measurement unit 109.

The area detector 101 transmits data indicative of coordinates or location and brightness of pixels located in the detected high brightness pixel area, to the maximum brightness detector 102, the calculator 103, the first counter 104, the second counter 105, and the second measurement unit 109.

The second measurement unit 109 includes a memory (not illustrated) storing parameters, programs, and so on. Specifically, the second measurement unit 109 stores a program and parameters for calculating a diameter of a particle in accordance with the equation of Rayleigh scattering, and a threshold diameter to which a calculated diameter is to be compared.

The threshold diameter is determined in accordance with a design rule of a semiconductor device to be fabricated, such as ultra-LSI. For instance, the threshold diameter is designed to be equal to or slightly smaller than a minimum diameter among diameters of wirings formed in a semiconductor device to be fabricated.

The second measurement unit 109 calculates an intensity of the scattered laser beam 150, based on a brightness indicated in the data transmitted from the area detector 101. A relation between a brightness and an intensity of a scattered laser beam has been determined by conducting an experiment in which there was used a laser beam source transmitting a laser beam having a known intensity, and is in advance stored in the second measurement unit 109.

The second measurement unit 109 calculates a diameter of a particle in accordance with the thus calculated intensity of the scattered laser beam 150 and the equation of Rayleigh scattering. Then, the second measurement unit 109 judges whether a calculated diameter is greater than the threshold diameter, or whether a calculated diameter is such a diameter that a resultant semiconductor device will have a defectiveness. If the calculated diameter is greater than the threshold diameter, the second measurement unit 109 transmits a stop signal to the chamber 120, namely, instructs the chamber 120 to stop fabrication of a semiconductor device.

An operation of the particle monitoring system in accordance with the second embodiment other than the above-mentioned operation is the same as the operation of the particle monitoring system in accordance with the first embodiment.

Hereinbelow is explained an operation of the computer 100 when the second measurement unit 109 calculates a diameter of a particle.

First, a user of the particle monitoring system actuates a predetermined key in the keyboard or input interface 107. In response to the actuation of the predetermined key, the input interface 107 transmits a signal to the laser beam source 110 to instruct the laser beam source 110 to radiate the laser beams 140. Then, the laser beam source 110 radiates the laser beams 140 to the chamber 120.

The laser beams 140 introduced into the chamber 120 through the first window 121 would be scattered, if the particles 160 exist on an optical path of the laser beams 140. The scattered laser beam 150 leaves the chamber 120 through the second window 122, and is received in the photodetector 130.

The scattered laser beam 150 is received in the photodetector 130 comprised of a charge coupled device (CCD) camera, and is output to the computer 100 as two-dimensional image data.

Figure 7:
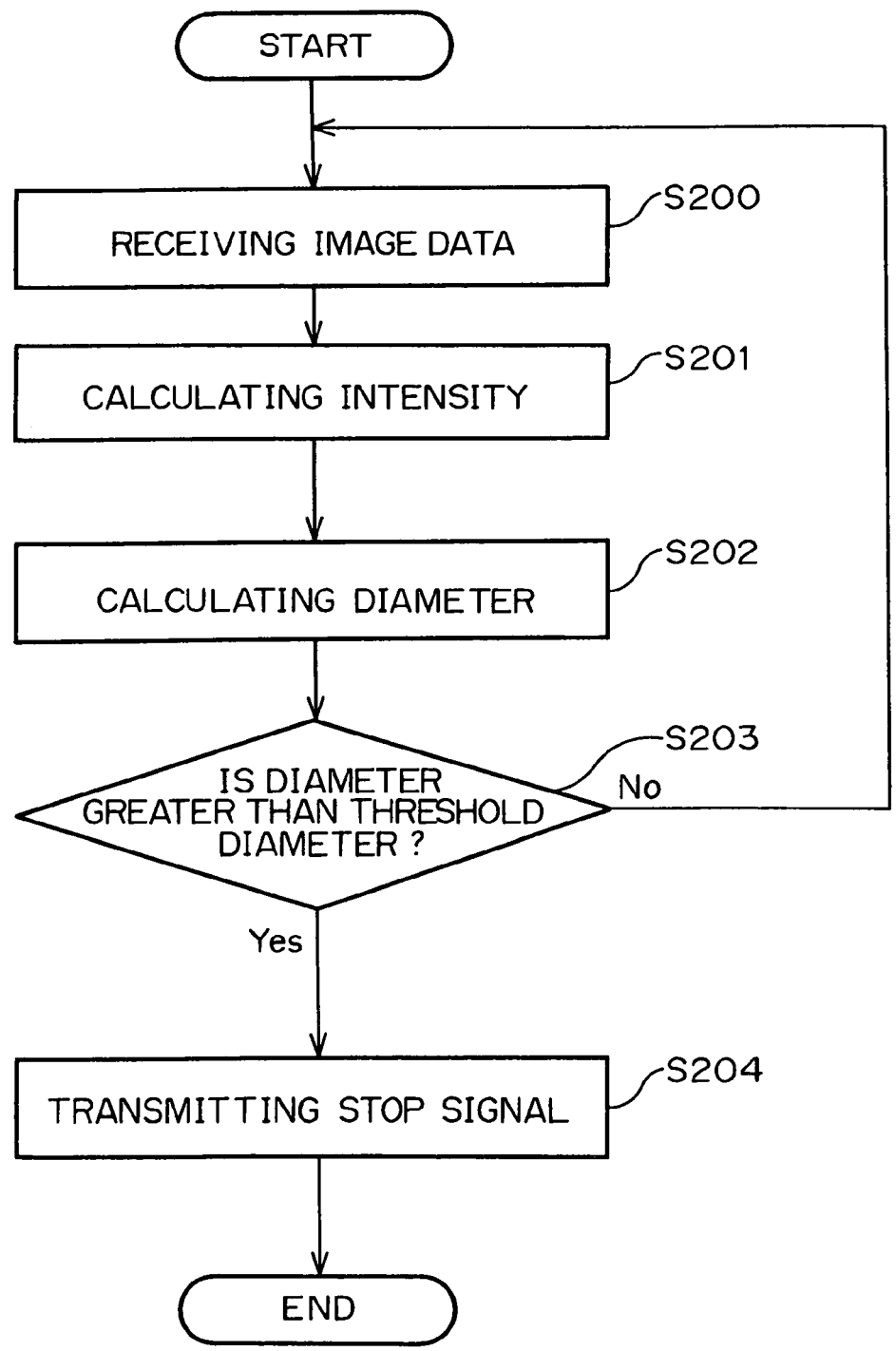
FIG. 7 is a flow chart of calculation of a diameter of a particle to be carried out by a computer constituting the particle monitor system in accordance with the second embodiment.

FIG. 7 is a flow-chart showing an operation of calculating a diameter of a particle, carried out by the computer 100.

First, the area detector 101 receives the two-dimensional image data transmitted to the computer 100 from the photodetector 130, in step S200.

Then, the area detector 101 detects location or coordinates and brightness of pixels having a brightness equal to or greater than the threshold brightness, and transmits data about the thus detected coordinates and brightness of the pixels, to the second measurement unit 109.

The second measurement unit 109 calculates an intensity of the scattered laser beam, based on the data transmitted from the area detector 101, in step S201.

Then, the second measurement unit 109 calculates a diameter of a particle, based on the thus calculated intensity of the scattered laser beam 150 and the equation of Rayleigh scattering, in step S202. Calculation for determining a diameter is explained later in detail.

Then, the second measurement unit 109 judges whether the thus calculated diameter is greater than the threshold diameter which was in advance stored in the second measurement unit 109. That is, the second measurement unit 109 judges whether a particle generated in the chamber 120 has such a size that a resultant semiconductor device would have a defectiveness, in step S203.

If the second measurement unit 109 judges that the calculated diameter is smaller than the threshold diameter, that is, the second measurement unit 109 judges that a particle generated in the chamber 120 does not have such a size that a resultant semiconductor device would have a defectiveness (NO in step S203), the second measurement unit 109 does not transmit a stop signal to the chamber 120. Hence, semiconductor devices are kept fabricated in the chamber 120.

Hence, next two-dimensional image data is input into the computer 100 from the photodetector 130. That is, the computer 100 returns to the step S200, and repeatedly carries out the above-mentioned steps S200 to 203.

If the second measurement unit 109 judges that the calculated diameter is equal to or greater than the threshold diameter, that is, the second measurement unit 109 judges that a particle generated in the chamber 120 has such a size that a resultant semiconductor device would have a defectiveness (YES in step S203), the second measurement unit 109 transmits a stop signal to the chamber 120, in step S204. Hence, semiconductor devices are no more fabricated in the chamber 120.

Thus, the operation of calculating a diameter of a particle, carried out by the computer 100, is over.

Hereinbelow is explained calculation of a diameter of a particle to be carried out by the second measurement unit 109 in step S202.

The equation of Rayleigh scattering used for calculation of a diameter of a particle is defined as follows.

$$I_1 = [(1+\cos^2\theta)/2/R^2] \times [2\pi/\lambda]^4 \times |(M^2-2)/(M^2+2)|^2 \times [A/2]^6 \times I_0$$

In the equation, $I_0$ indicates an intensity of an incident laser beam, $I_1$ indicates an intensity of a scattered laser beam, θ indicates an angle formed between the incident laser beam and the detected, scattered laser beam, R indicates a distance from a location at which the laser beam is scattered, to a location at which the scattered laser beam is detected, λ indicates a wavelength of the incident laser beam, M indicates an index of refraction, and a indicates A diameter of a particle.

The parameters $I_0$, θ, R, λ and M are in advance input into the second measurement unit 109. The intensity $I_1$ is calculated by the second measurement unit 109 in accordance with the above-mentioned equation.

It should be noted that a brightness of the scattered laser beam, detected by the photodetector 130, that is, an intensity of the scattered laser beam, calculated by the second measurement unit 109 is slightly different from an actual intensity of the scattered laser beam due to a sensitivity of the detection system such as the photodetector 130. Accordingly, it is necessary to prepare a proportion constant S for compensating for such a sensitivity of the detection system. The proportion constant S can be determined by measuring a diameter of a particle having a known diameter, and comparing the measured diameter to an actual diameter.

Specifically, the proportion constant S is defined as follows.

$$S = Q \times 5 / I$$

In the equation, Q indicates a maximum brightness of a laser beam scattered by a particle having a known diameter which laser beam has a known intensity, and I indicates an intensity of a scattered laser beam.

Based on the above-mentioned equations and parameters, it is possible to calculate a diameter of a particle generated in the chamber 120. As mentioned above, the second measurement unit 109 calculates an intensity of a scattered laser beam, and compensates for the thus calculated intensity with the above-mentioned proportion constant S. Accordingly, the thus obtained diameter of a particle is not a relative diameter, but an actual diameter of a particle generated in the chamber 120.

If the thus obtained diameter of a particle is greater than the threshold diameter, fabrication of a semiconductor device is made to stop, ensuring prevention of fabrication of defective semiconductor devices. Thus, a fabrication yield in fabrication of a semiconductor device can be enhanced.

Hereinbelow are shown the results of the experiment in which YAG (yttrium aluminum garnet) laser was radiated at double harmonic to a particle of titanium generated in the chamber 120, and a diameter of the particle was measured by means of the photodetector 130 including a CCD camera.

In the experiment, the parameters are as follows.

$\theta = 90$ degrees
$R = 1$ m
$\lambda = 532$ nm
$M = 3.48 + 2.27I$
$I_0 = 4298$ W/cm$^2$
$S = 6.2 \times 10^{14}$ Based on these parameters and the above-mentioned equations, a particle of titanium generated in the chamber 120 was calculated to be 21 nm.

Figure 8A:
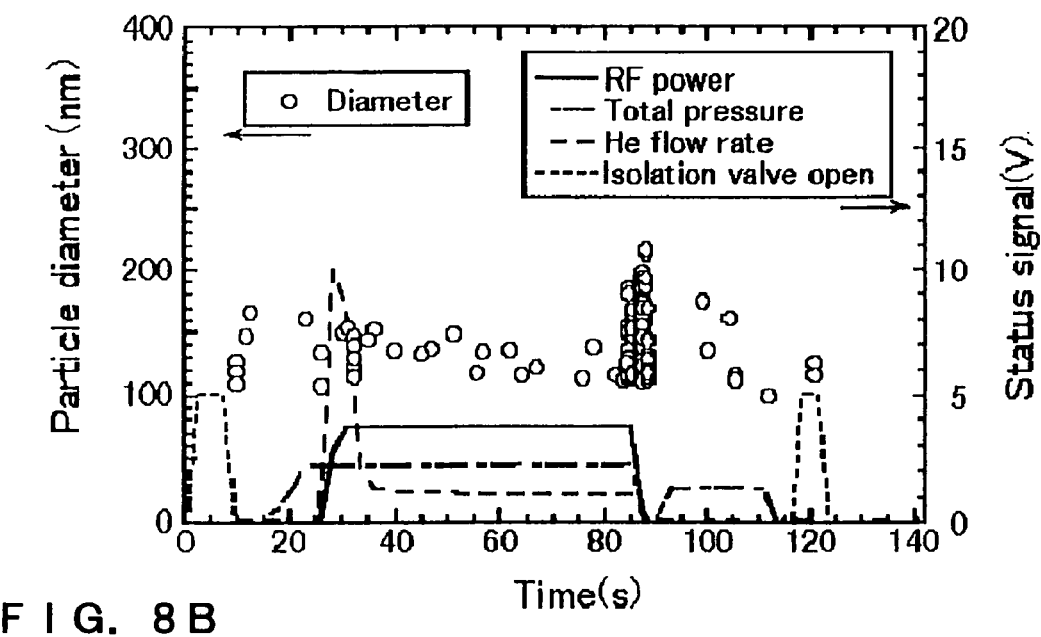
FIGS. 8A and 8B illustrate results of measurement of diameters of particles.
Figure 8B:
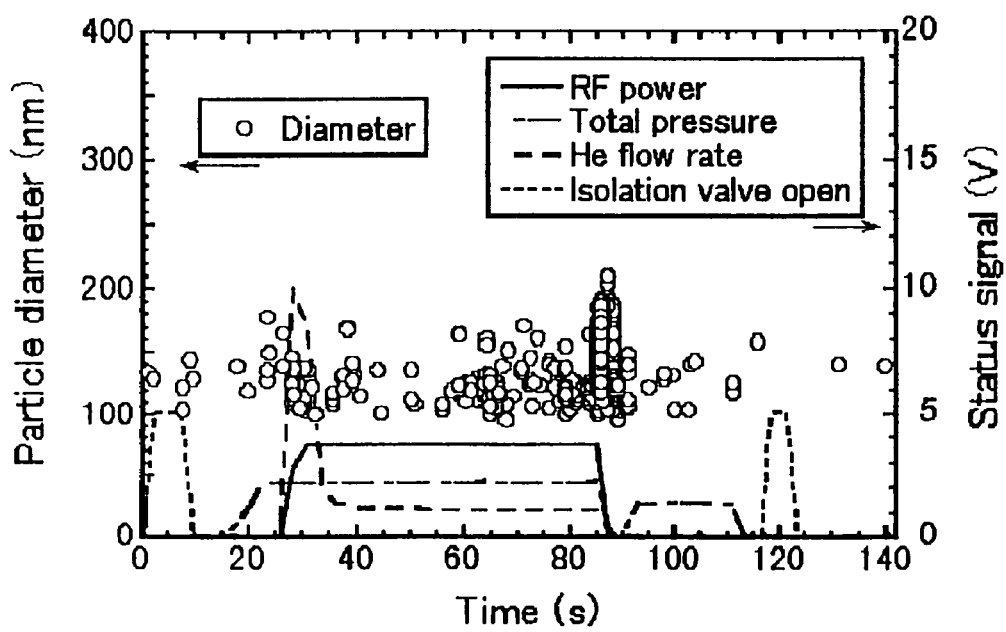

FIGS. 8A and 8B are graphs obtained by plotting diameters of particles. The diameters were measured while semiconductor devices are being fabricated. In FIGS. 8A and 8B, hollow circles indicate a diameter of a particle, and a solid line and a broken line indicate a status signal which indicates a status of an operation of an apparatus for fabricating a semiconductor device. The axes of abscissa in FIGS. 8A and 8B indicate a time in the unit of a second.

It is understood how a diameter of a particle generated in the chamber 120 while a semiconductor device is being fabricated varies in view of FIGS. 8A and 8B. The thus obtained diameter of a particle is helpful for researching the reason why a particle is generated.

By carrying out the above-mentioned measurement using various particles each having a known diameter, it would be possible to know a lower limit of detection by the particle monitoring system, that is, how small size of a particle the particle monitoring system can detect.

Figure 9:
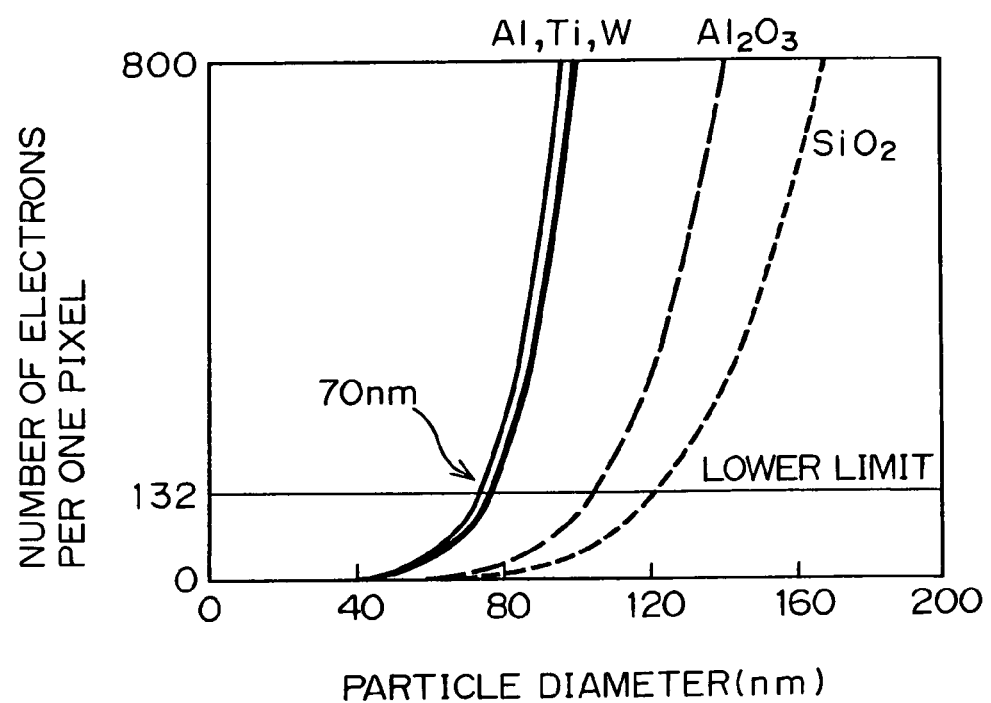
FIG. 9 is a graph showing a lower limit below which a particle diameter cannot be detected in the particle monitor system.

FIG. 9 shows a lower limit of detection in the particle monitoring system.

In FIG. 9, an axis of ordinate indicates the number of electrons generated by a scattered laser beam, per a pixel of a CCD camera constituting the photodetector 130, and an axis of abscissa indicates a size of a particle. In FIG. 9, particles composed of aluminum (Al), titanium (Ti), tungsten (W), Al$_2$O$_3$ (aluminum dioxide) and SiO$_2$ (silicon dioxide) are used. Since the number of electrons per a pixel of the CCD camera is in proportion to a brightness of the pixel, the number can be calculated based on a brightness or an intensity of a scattered laser beam.

A lower limit of detection in the particle monitoring system can be defined as a point at which an actual size of a particle is not coincident with a measured size of a particle, even if a range of error is taken into consideration.

Specifically, as illustrated in FIG. 9, as a size of a particle becomes smaller, the number of electrons per a pixel of the CCD camera becomes smaller. If the number of electrons becomes smaller than a certain number, which is equal to 132 in FIG. 9, the scattered laser beam 150 might not be distinguished from background noises, or a size of a particle could not be accurately measured.

Thus, by knowing a lower limit of detection in the particle monitoring system, it would be possible to fabricate a particle monitoring system having an optimal limit of detection in dependence on specific semiconductor devices to be fabricated. In addition, conditions under which a semiconductor device is to be fabricated may be varied in accordance with a lower limit of detection in the particle monitoring system.

When the first measurement unit 106 measures a relative size of a particle, there may be used a maximum brightness, a total of brightness, and the number of pixels which were obtained in previous measurements, as threshold values, in place of the threshold values input from the input interface 107.

As an alternative, when the first measurement unit 106 measures a relative size of a particle, there may be used a maximum brightness, a total of brightness, and the number of pixels which are obtained in an experiment in which a particle having a know size is used, as threshold values, in place of the threshold values input from the input interface 107. By doing so, a size of a particle indicates an actual size of a particle.

If the first measurement unit 106 stores a maximum brightness, a total of brightness, and the number of pixels in a memory, it would be possible to know a size and the number of particles generated in a certain period of time. Hence, static about a size and the number of particles can be obtained, and the static may be used to research the reason why particles are generated and how particles are generated.

In the above-mentioned embodiments, the input interface 107 transmits a finish signal when the steps of detecting pixels having a brightness equal to or greater than the threshold brightness are to be finished. The input interface 107 may be designed to include a timer such that a finish signal is automatically transmitted when a predetermined period of time has passed.

In the above-mentioned embodiments, the computer 100 is designed to include the maximum brightness detector 102, the calculator 103 and the first counter 104, however, it should be noted that the computer 100 may be designed to include one or two of the maximum brightness detector 102, the calculator 103 and the first counter 104.

As an alternative, by varying a weighing factor which the first measurement unit 106 uses when a relative size of a particle is measured, only one or two of the maximum brightness detector 102, the calculator 103 and the first counter 104 may operate. However, it would be possible to accurately measure a relative size of a particle by optimally combining and using data transmitted from the maximum brightness detector 102, the calculator 103 and the first counter 104.

A relative size of a particle may be measured by the first measurement unit 106 not only by multiplying a size obtained from the maximum brightness, a total of brightness, or the number of pixel by a weighing factor to thereby have an average, but also by other methods. For instance, a relative size of a particle may be calculated first by calculating an average of a relative size obtained from the maximum brightness and a relative size obtained from a total of brightness, and secondly by calculating an average of the thus calculated average and a relative size obtained from the number of pixels.

Since the laser beam 140 is scattered in different manners in dependence not only on a size of a particle, but also on a shape of a particle, it would be possible to accurately measure a size of a particle by processing data about pixels having a brightness equal to or greater than a threshold brightness, taking a shape of a particle into consideration.

The laser beam source 110 may be designed to include a driver for scanning the laser beams 140 in a predetermined area.

The display 108 may be designed to have a speaker to aurally annunciate the number and a size of particles to a user.

In the above-mentioned second embodiment, the maximum brightness detector 102 may be designed to transmit a maximum brightness to both the first measurement unit 106 and the second measurement unit 109, and the second measurement unit 109 may be designed to calculate an intensity of the scattered laser beam 150, based on the maximum brightness transmitted from the first measurement unit 106. However, in order to accomplish such an arrangement, it should be noted that a relation between a maximum brightness and an intensity of a scattered laser beam has to be in advance determined, and has to be stored in the second measurement unit 109.

As mentioned above, it is possible to calculate a relative size of a particle, based on an intensity of a scattered laser beam which intensity is calculated based on the above-mentioned relation.

A diameter of a particle measured by the second measurement unit 109, and a message indicating that a stop signal has been transmitted to the chamber 120 may be displayed in the display 108 to annunciate to a user of the particle monitoring system.

In the second embodiment, when fabrication of a semiconductor device is stopped due to a greater diameter of a particle than the threshold diameter, a furnace in the chamber 120 may be heated to thereby remove reaction by-products. By heating a furnace, it is ensured that reaction by-products cannot exist in the chamber 120 in an amount equal to or greater than a certain amount, further ensuring that it would be possible to suppress generation of particles in an amount smaller than a certain amount. As a result, it is possible to enhance a yield of fabricating a semiconductor device.

The above-mentioned particle monitoring system may be accomplished as a program including various commands, and be presented through a recording medium readable by a computer.

Figure 10:
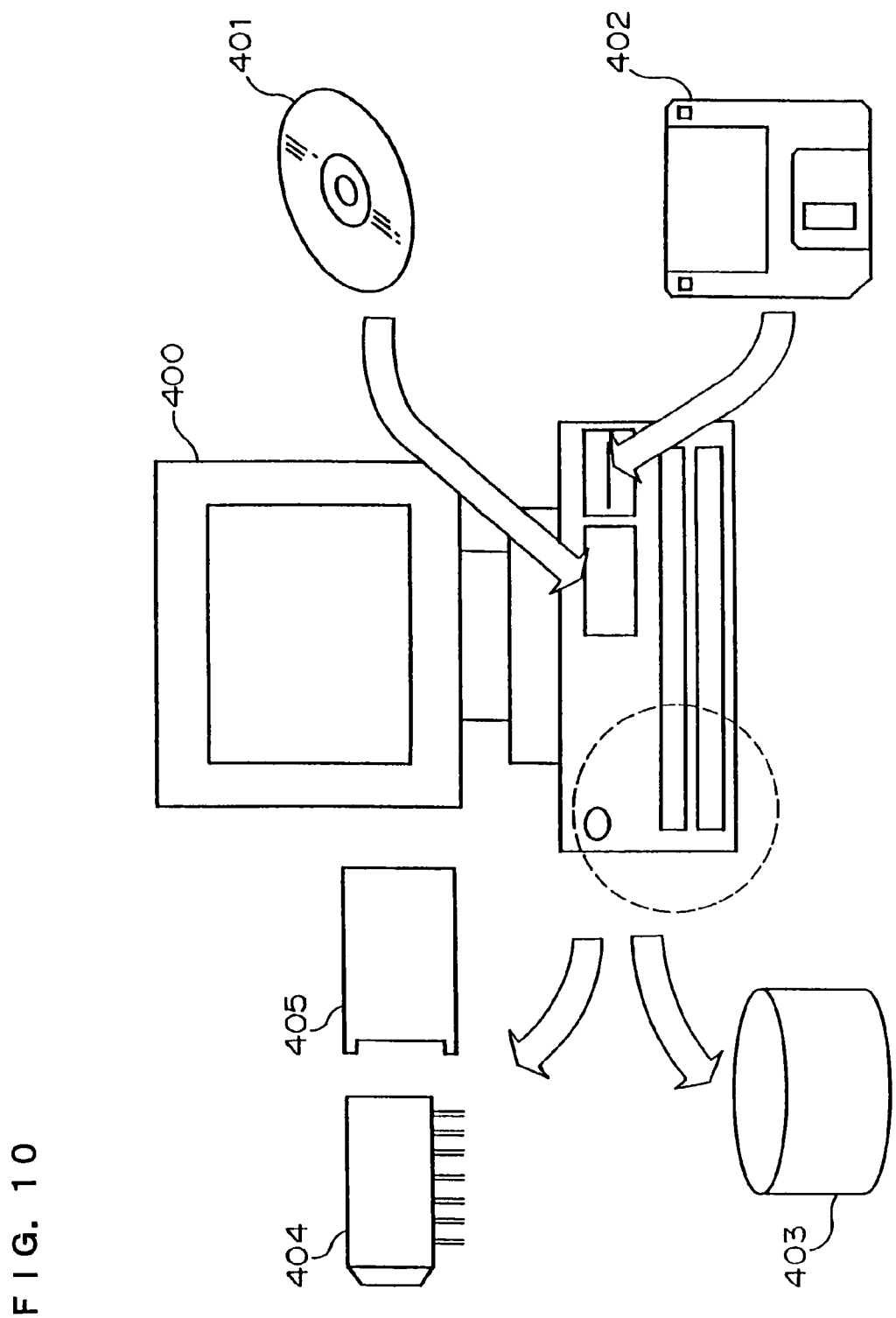
FIG. 10 illustrates examples of recording mediums in which a program for monitoring particles is to be stored.

In the specification, the term "recording medium" means any medium which can record data therein. Examples of a recording medium are illustrated in FIG. 10.

The term "recording medium" includes, for instance, a disk-shaped recorder 401 such as CD-ROM (Compact Disk-ROM) or PD, a magnetic tape, MO (Magneto Optical Disk), DVD-ROM (Digital Video Disk-Read Only Memory), DVD-RAM (Digital Video Disk-Random Access Memory), a floppy disk 402, a memory chip 404 such as RAM (Random Access Memory) or ROM (Read Only Memory), EPROM (Erasable Programmable Read Only Memory), EEPROM (Electrically Erasable Programmable Read Only Memory), smart media (Registered Trade Mark), a flush memory, a rewritable card-type ROM 405 such as a compact flush card, a hard disk 403, and any other suitable means for storing a program therein.

A recording medium storing a program for accomplishing the above-mentioned apparatus may be accomplished by programming functions of the above-mentioned apparatuses with a programming language readable by a computer, and recording the program in a recording medium such as mentioned above.

A hard disc equipped in a server may be employed as a recording medium. It is also possible to accomplish the recording medium in accordance with the present invention by storing the above-mentioned computer program in such a recording medium as mentioned above, and reading the computer program by other computers through a network.

As a computer 400, there may be used a personal computer, a desk-top type computer, a note-book type computer, a mobile computer, a lap-top type computer, a pocket computer, a server computer, a client computer, a workstation, a host computer, a commercially available computer, and electronic exchanger, for instance.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Applications Nos. 10-259532 and 11-255320 filed on Sep. 14, 1998 and Sep. 9, 1999, respectively, including specification, claims, drawings and summary is incorporated herein by reference in its entirety.

What is claimed is:

1. An apparatus for monitoring a size of a particle, comprising:
   a laser beam source which radiates a laser beam to an area in which particles exist;
   a photodetector which is comprised of a plurality of pixels, which receives said laser beam having been scattered by said particles, and outputs image data including brightness of pixels; and
   an area detector which determines as a group only pixels that are simultaneously irradiated by said laser beam scattered by one of said particles, that are located adjacent to each other, and that have a brightness equal to or greater than a predetermined threshold brightness.

2. The apparatus as set forth in claim 1, further comprising:
   a maximum brightness detector which detects a maximum brightness among levels of brightness of pixels in said group; and
   a measurement unit which compares said maximum brightness to said predetermined threshold brightness to thereby measure a relative size of said particles.

3. The apparatus as set forth in claim 1, further comprising:
   a maximum brightness detector which detects a maximum brightness among levels of brightness of pixels in said group; and
   a measurement unit which measures an intensity of said scattered laser beam, based on said maximum brightness, and measures a relative size of said particles, based on said intensity of said scattered laser beam, in accordance with an equation which defines a relation between an intensity of a scattered laser beam and a relative size of particles.

4. The apparatus as set forth in claim 3, wherein said particles are generated in fabrication of a semiconductor device, and further comprising a third measurement unit which judges whether a relative size of said particles is greater than a predetermined threshold size in order to judge whether said particles would exert harmful influence on a semiconductor device, and which ceases fabrication of a semiconductor device, if said relative size of said particles has been judged to be greater than said predetermined threshold size.

5. The apparatus as set forth in claim 1, further comprising a scanner which scans said laser beam emitted from said laser beam source.

6. The apparatus as set forth in claim 1, wherein said photodetector includes a charge coupled device camera comprised of a plurality of light-receiving devices arranged in a matrix.

7. The apparatus as set forth in claim 2, further comprising a counter which counts up a number of said groups.

8. The apparatus as set forth in claim 1, further comprising a heater for heating a chamber in which said particle is generated, to remove by-products from said chamber.

9. The apparatus as set forth in claim 1, further comprising:
a counter which counts a number of pixels in said group; and
a measurement unit which compares said number to a predetermined threshold number to thereby measure a relative size of said particles.

10. The apparatus as set forth in claim 1, further comprising a counter which counts up a number of said groups.

11. The apparatus as set forth in claim 9, further comprising a scanner which scans said laser beam emitted from said laser beam source.

12. The apparatus as set forth in claim 9, wherein said photodetector includes a charge coupled device camera comprised of a plurality of light-receiving devices arranged in a matrix.

13. The apparatus as set forth in claim 9, further comprising a counter which counts up a number of said groups.

14. The apparatus as set forth in claim 9, further comprising a heater for heating a chamber in which said particle is generated, to remove by-products from said chamber.

15. The apparatus as set forth in claim 1, further comprising:
a calculator which calculates a total of brightness of pixels in said group; and
a measurement unit which compares said total to a predetermined threshold total to thereby measure a relative size of said particles.

16. The apparatus as set forth in claim 1, further comprising:
a maximum brightness detector which detects a maximum brightness among levels of brightness of pixels in said group;
a counter which counts a number of pixels in said group; and
a measurement unit which compares said maximum brightness or said number to a predetermined threshold brightness or a predetermined threshold number to thereby measure a relative size of said particles.

17. The apparatus as set forth in claim 1, further comprising:
a maximum brightness detector which detects a maximum brightness among levels of brightness of pixels in said group;
a counter which counts a number of pixels in said group;
a calculator which calculates a total of brightness of pixels in said group; and
a measurement unit which uses at least one of said total and said maximum brightness and said number in order to measure a relative size of said particles.

18. The apparatus as set forth in claim 15, further comprising a scanner which scans said laser beam emitted from said laser beam source.

19. The apparatus as set forth in claim 15, wherein said photodetector includes a charge coupled device camera comprised of a plurality of light-receiving devices arranged in a matrix.

20. The apparatus as set forth in claim 15, further comprising a counter which counts up a number of said groups.

21. The apparatus as set forth in claim 15, further comprising a heater for heating a chamber in which said particle is generated, to remove by-products from said chamber.

22. The apparatus as set forth in claim 1, further comprising:
a first measurement unit which measures an intensity of said scattered laser beam, based on brightness of pixels in said group; and
a second measurement unit which measures a relative size of said particles, based on said intensity of said scattered laser beam, in accordance with an equation which defines a relation between an intensity of a scattered laser beam and a relative size of particles.

23. The apparatus as set forth in claim 22, wherein said first measurement unit comprises a maximum brightness detector which detects a maximum brightness among levels of brightness of pixels in said group, and said first measurement unit measures an intensity of said scattered laser beam, based on said maximum brightness.

24. The apparatus as set forth in claim 22, wherein said particles are generated in fabrication of a semiconductor device, and further comprising a third measurement unit which judges whether a relative size of said particles is greater than a predetermined threshold size in order to judge whether said particles would exert harmful influence on a semiconductor device, and which ceases fabrication of a semiconductor device, if said relative size of said particles has been judged to be greater than said predetermined threshold size.

25. The apparatus as set forth in claim 22, further comprising a scanner which scans said laser beam emitted from said laser beam source.

26. The apparatus as set forth in claim 22, wherein said photodetector includes a charge coupled device camera comprised of a plurality of light-receiving devices arranged in a matrix.

27. The apparatus as set forth in claim 22, further comprising a counter which counts up a number of said groups.

28. The apparatus as set forth in claim 22, wherein said second measurement unit includes a memory which stores a software program used for calculating a size of a particle in accordance with the equation of Rayleigh scattering, and a threshold size to which a calculated size is to be compared.

29. The apparatus as set forth in claim 28, wherein said threshold size is equal to or smaller than a minimum diameter among diameters of wirings in a semiconductor device to be fabricated.

30. The apparatus as set forth in claim 22, further comprising a heater for heating a chamber in which said particle is generated, to remove by-products from said chamber.

31. A method of monitoring a size of a particle, comprising:
radiating a laser beam to an area in which particles exist;
receiving said laser beam having been scattered by said particles with a photodetector comprised of a plurality of pixels, and creating image data including brightness of said pixels; and
determining as a group only pixels that are simultaneously irradiated by said laser beam scattered by one of said particles, that are located adjacent to each other, and that have a brightness equal to or greater than a predetermined threshold brightness.

32. The method as set forth in claim 31, further comprising:
detecting a maximum brightness among levels of brightness of pixels in said group; and
comparing said maximum brightness to a predetermined threshold brightness to thereby measure a relative size of said particles.

33. The method as set forth in claim 31, further comprising:
detecting a maximum brightness among levels of brightness of pixels in said group; and
measuring an intensity of said scattered laser beam based on said maximum brightness.

34. The method as set forth in claim 33, wherein said particles are generated in fabrication of a semiconductor device, and further comprising the steps of:
judging whether a relative size of said particles is greater than a predetermined threshold size in order to judge whether said particles would exert harmful influence on a semiconductor device; and
ceasing fabrication of a semiconductor device, if said relative size of said particles has been judged to be greater than said predetermined threshold size.

35. The method as set forth in claim 34, further comprising the step of heating a chamber in which said particles are generated, for removing by-products from said chamber.

36. The method as set forth in claim 31, further comprising the step of scanning said laser beam.

37. The method as set forth in claim 32, further comprising:
counting up a number of said groups.

38. The method as set forth in claim 31, comprising:
counting a number of pixels in said group; and
comparing said number to a predetermined threshold number to thereby measure a relative size of said particles.

39. The method as set forth in claim 38, further comprising the step of scanning said laser beam.

40. The method as set forth in claim 38, further comprising counting up a number of said groups.

41. The method as set forth in claim 31, comprising:
calculating a total of brightness of pixels in said group; and
comparing said total to a predetermined threshold brightness to thereby measure a relative size of said particles.

42. The method as set forth in claim 41, wherein said particles are generated in fabrication of a semiconductor device, and further comprising the steps of:
judging whether said relative size of said particles is greater than a predetermined threshold size in order to judge whether said particles would exert harmful influence on a semiconductor device; and
ceasing fabrication of a semiconductor device, if said relative size of said particles has been judged to be greater than said predetermined threshold size.

43. The method as set forth in claim 41, further comprising the step of heating a chamber in which said particles are generated, for removing by-products from said chamber.

44. The method as set forth in claim 41, further comprising the step of scanning said laser beam.

45. The method as set forth in claim 41, further comprising counting up a number of said groups.

46. The method as set forth in claim 41, further comprising storing a software program used for calculating a size of a particle in accordance with the equation of Rayleigh scattering, and a threshold size to which a calculated size is to be compared.

47. The method as set forth in claim 46, wherein said threshold size is equal to or smaller than a minimum diameter among diameters of wirings in a semiconductor device to be fabricated.

48. The method as set forth in claim 31, comprising:
measuring an intensity of said scattered laser beam, based on brightness of pixels in said group; and
measuring a relative size of said particles, based on said intensity of said scattered laser beam, in accordance with an equation which defines a relation between an intensity of a scattered laser beam and a relative size of particles.

49. The method as set forth in claim 48, wherein said particles are generated in fabrication of a semiconductor device, and further comprising the steps of:
judging whether said relative size of said particles is greater than a predetermined threshold size in order to judge whether said particles would exert harmful influence on a semiconductor device; and
ceasing fabrication of a semiconductor device, if said relative size of said particles has been judged to be greater than said predetermined threshold size.

50. The method as set forth in claim 49, further comprising the step of heating a chamber in which said particles are generated, for removing by-products from said chamber.

51. The method as set forth in claim 48, further comprising the step of scanning said laser beam.

52. The method as set forth in claim 48, further comprising counting up a number of said groups.

53. The method as set forth in claim 48, further comprising the step of storing a software program used for calculating a size of a particle in accordance with the equation of Rayleigh scattering, and a threshold size to which a calculated size is to be compared.

54. The method as set forth in claim 53, wherein said threshold size is equal to or smaller than a minimum diameter among diameters of wirings in a semiconductor device to be fabricated.

55. A recording medium readable by a computer, storing a program therein for causing a computer to act as an apparatus for monitoring a size of a particle, said apparatus comprising:
a laser beam source which radiates a laser beam to an area in which particles exist;
a photodetector which is comprised of a plurality of pixels, wherein said photodetector receives said laser beam having been scattered by said particles, and outputs image data including brightness of pixels; and
an area detector which determines as a group only pixels that are simultaneously irradiated by said laser beam scattered by one of said particles, that are located adjacent to each other, and that have a brightness equal to or greater than a predetermined threshold brightness.

56. The recording medium as set forth in claim 55, wherein said apparatus further comprises:
a maximum brightness detector which detects a maximum brightness among levels of brightness of pixels in said group; and
a measurement unit, which compares said maximum brightness to a predetermined threshold brightness to thereby measure a relative size of said particles.

57. The recording medium as set forth in claim 55, wherein said apparatus further comprises:
a maximum brightness detector which detects a maximum brightness among levels of brightness of pixels in said group; and
a measurement unit which measures an intensity of said scattered laser beam, based on said maximum brightness, and measures a relative size of said particles, based on said intensity of said scattered laser beam, in accordance with an equation which defines a relation between an intensity of a scattered laser beam and a relative size of particles.

58. The recording medium as set forth in claim 55, wherein said particles are generated in fabrication of a semiconductor device, and wherein said apparatus further includes a measurement unit which judges whether a relative size of said particles is greater than a predetermined threshold size in order to judge whether said particles would exert harmful influence on said semiconductor device, and which ceases fabrication of said semiconductor device, if said relative size of said particles has been judged to be greater than said predetermined threshold size.

59. The recording medium as set forth in claim 55, wherein said apparatus further includes a particle counter which counts up each time said particle counter receives a signal from said area detector, and transmits a signal indicative of a count, to a measurement, unit.

60. The recording medium as set forth in claim 55, wherein said apparatus further includes a heater for heating a chamber in which said particle is generated, to remove by-products from said chamber.

61. The recording medium as set forth in claim 55, wherein said apparatus further includes a counter which counts up a number of said groups.

62. The recording medium as set forth in claim 55, wherein said apparatus further includes:
a counter which counts a number of pixels in said group; and
a measurement unit which compares said number to a predetermined threshold number to thereby measure a relative size of said particles.

63. The recording medium as set forth in claim 55, wherein said apparatus further includes a scanner which scans said laser beam emitted from said laser beam source.

64. The recording medium as set forth in claim 55, wherein said photodetector includes a charge coupled device camera comprised of a plurality of light-receiving devices arranged in a matrix.

65. The recording medium as set forth in claim 55, wherein said apparatus further includes:
a calculator which calculates a total of brightness of pixels in said group; and
a measurement unit which compares said total to a predetermined threshold total to thereby measure a relative size of said particles.

66. The recording medium as set forth in claim 55, wherein said apparatus further includes:
a maximum brightness detector which detects a maximum brightness among levels of brightness of pixels in said group;
a counter which counts a number of pixels in said group; and
a measurement unit which compares said maximum brightness or said number to a predetermined threshold brightness, or a predetermined threshold number, to thereby measure a relative size of said particles.

67. The recording medium as set forth in claim 55, wherein said apparatus further includes:
a maximum brightness detector which detects a maximum brightness among levels of brightness of pixels in said group;
a counter which counts a number of pixels in said group;
a calculator which calculates a total of brightness of pixels in said group; and
a measurement unit which uses at least one of said total and said maximum brightness and said number in order to measure a relative size of said particles.

68. The recording medium as set forth in claim 55, wherein said apparatus further includes:
a first measurement unit which measures an intensity of said scattered laser beam, based on brightness of pixels in said group; and
a second measurement unit which measures a relative size of said particles, based on said intensity of said scattered laser beam, in accordance with an equation which defines a relation between an intensity of a scattered laser beam and a relative size of particles.

69. The recording medium as set forth in claim 68, wherein said first measurement unit comprises a maximum brightness detector which detects a maximum brightness among levels of brightness of pixels in said group, and said first measurement unit measures an intensity of said scattered laser beam, based on said maximum brightness.

70. The recording medium as set forth in claim 68, wherein said second measurement unit includes a memory which stores a software program used for calculating a size of a particle in accordance with the equation of Rayleigh scattering, and a threshold size to which a calculated size is to be compared.

71. A recording medium readable by a computer, storing a program therein for causing a computer to carry out a method of monitoring a size of a particle, said method comprising:
radiating a laser beam to an area in which particles exist;
receiving said laser beam having been scattered by said particles; and
determining as a group only pixels that are simultaneously irradiated by said laser beam scattered by one of said particles, that are located adjacent to each other, and that have a brightness equal to or greater than a predetermined threshold brightness.

72. The recording medium as set forth in claim 71, wherein said method further includes:
detecting a maximum brightness among levels of brightness of pixels in said group; and
comparing said maximum brightness to a predetermined threshold brightness to thereby measure a relative size of said particles.

73. The recording medium as set forth in claim 71, wherein said method further includes:
detecting a maximum brightness among levels of brightness of pixels in said group; and measuring an intensity of said scattered laser beam, based on said maximum brightness.

74. The recording medium as set forth in claim 71, wherein said particles are generated in fabrication of a semiconductor device, and wherein said method further includes:
   judging whether a relative size of said particles is greater than a predetermined threshold size in order to judge whether said particles would exert harmful influence on said semiconductor device; and
   ceasing fabrication of said semiconductor device, if said relative size of said particles has been judged to be greater than said predetermined threshold size.

75. The recording medium as set forth in claim 74, wherein said method further includes heating a chamber in which said particles are generated, for removing by-products from said chamber.

76. The recording medium as set forth in claim 71, wherein said method further includes counting up a number of said groups.

77. The recording medium as set forth in claim 71, wherein said method further includes:
   counting a number of pixels in said group; and
   comparing said number to a predetermined threshold number to thereby measure a relative size of said particles.

78. The recording medium as set forth in claim 71, wherein said method further includes scanning said laser beam.

79. The recording medium as set forth in claim 71, wherein said method further includes:
   calculating a total of brightness of pixels in said group; and
   comparing said total to a predetermined threshold brightness to thereby measure a relative size of said particles.

80. The recording medium as set forth in claim 71, wherein said method further includes storing a software program used for calculating a size of a particle in accordance with the equation of Rayleigh scattering, and a threshold size to which a calculated size is to be compared.

81. The recording medium a set forth in claim 71, wherein said method further includes:
   measuring an intensity of said scattered laser beam, based on brightness of pixels in said group; and
   measuring a relative size of said particles, based on said intensity of said scattered laser beam, in accordance with an equation which defines a relation between an intensity of a scattered laser beam and a relative size of particles.

* * * * *